US00PP36633P2

(12) United States Plant Patent
Rupp

(10) Patent No.: US PP36,633 P2
(45) Date of Patent: Apr. 29, 2025

(54) ***DIANTHUS* PLANT NAMED 'KLEDG23508'**

(50) Latin Name: ***Dianthus caryophyllus* L.**
Varietal Denomination: KLEDG23508

(71) Applicant: KLEMM + SOHN GMBH & CO. KG, Stuttgart (DE)

(72) Inventor: Judith Rupp, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/655,743

(22) Filed: May 6, 2024

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./272, 273
CPC ..... A01H 5/0233
See application file for complete search history.

(56) References Cited

PUBLICATIONS https://daigelis.lt/wp-content/uploads/2021/08/Dianthus-Selecta.pdf; Aug. 9, 2024; 2 pages.*
https://plantechnical.com/wp-content/uploads/2023/06/dianthus-se-2023-1-compressed-2081220.pdf; Aug. 9, 2024; 2 pages.*
https://huiskula.fi/luettelot/2025/selecta_neilikat_2024-2025.pdf; Aug. 9, 2024; 2 pages.*

* cited by examiner

*Primary Examiner* — Kent L Bell
(74) *Attorney, Agent, or Firm* — Weatherly IP Solutions, LLC; James M. Weatherly

(57) ABSTRACT

A new *Dianthus* plant designated 'KLEDG23508' particularly distinguished by dark purple flowers with a light border that change in appearance based on light intensity, is disclosed.

2 Drawing Sheets

Genus and species: *Dianthus caryophyllus* L.
Variety denominations: 'KLEDG23508'.

BACKGROUND

The present invention comprises a new and distinct variety of *Dianthus*, botanically known as *Dianthus caryophyllus* L, and hereinafter referred to by the variety name 'KLEDG23508'. 'KLEDG23508' originated from an open pollination from the proprietary female parent 'DSS-2017-7918' (unpatented) and an unknown male parent in 2018 between May and August in Stuttgart, Germany.

In June 2019, 'KLEDG23508' was first vegetatively propagated by vegetative stem cuttings in Stuttgart, Germany. 'KLEDG23508' was found to reproduce true to type in successive generations of asexual propagation in Stuttgart, Germany via vegetative stem cuttings.

SUMMARY

The following are the most outstanding and distinguishing characteristics of 'KLEDG23508' when grown under normal horticultural practices in Stuttgart, Germany.

1. Dark purple flowers with a light border that change in appearance based on light intensity.

DESCRIPTION OF THE PHOTOGRAPH

This new *Dianthus* plant is illustrated by the accompanying photographs taken in a greenhouse in Stuttgart, Germany. The colors shown are as true as can be reasonably obtained by conventional photographic procedures.

DESCRIPTION

Figure 1:
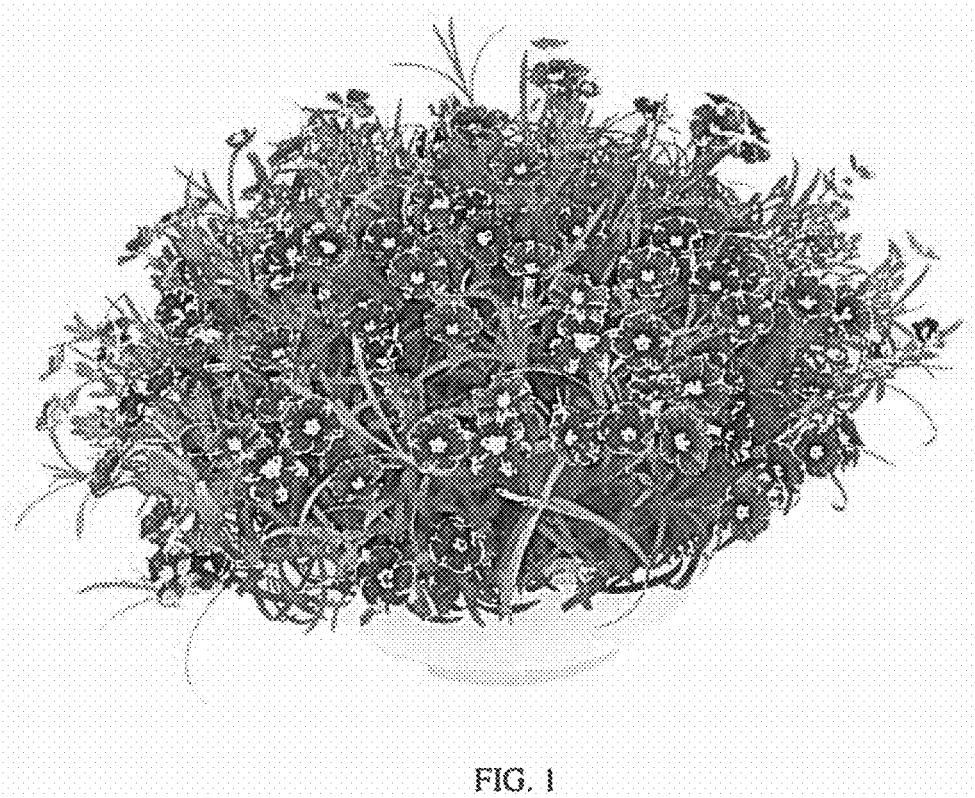
FIG. 1 is a photograph of a whole plant of the new *Dianthus* plant showing the foliage, buds and flower of a 17-week-old plant taken in February 2023.
Figure 2:
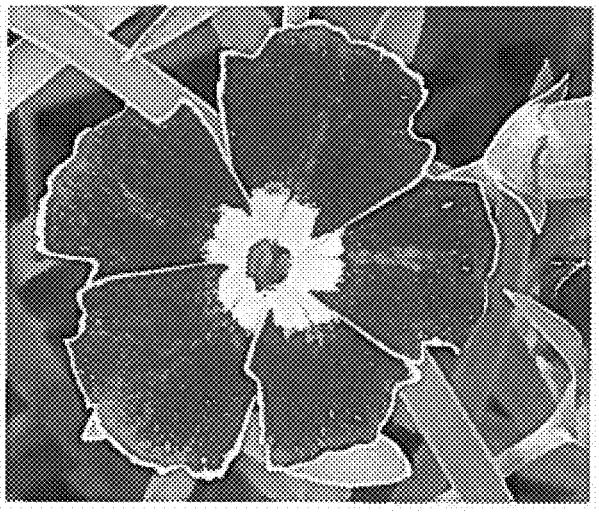
FIG. 2 is a photograph of a flower of the new *Dianthus* at 6 months old under low light conditions in a greenhouse in Stuttgart, Germany in April 2020.
Figure 3:
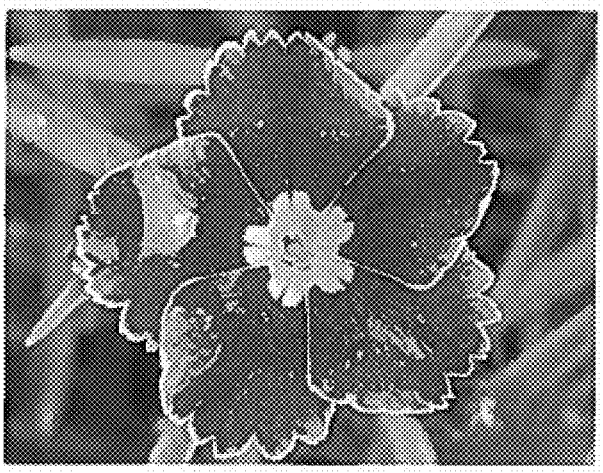
FIG. 3 is a photograph of flower of the new *Dianthus* plant at 2 months old under high light conditions in a greenhouse in Stuttgart, Germany in August 2020.

The following detailed descriptions set forth the distinctive characteristics of 'KLEDG23508'. The data which define these characteristics were collected from asexual reproductions carried out in Stuttgart, Germany. Data was collected in April 2024 on 6-month old plants grown in a plastic greenhouse. Color references are to The R.H.S. Colour Chart of The Royal Horticultural Society of London (R.H.S.), $5^{th}$ edition (2007).

Classification:

*Family*.—Caryophyllaceae.
*Botanical*.—*Dianthus caryophyllus* L.
*Common*.—Perennial carnation.
*Designation*.—'KLEDG23508'.

Parentage:

*Female parent*.—'DSS-207-7918'.
*Male parent*.—Unknown.

Plant:
*Propagation type*.—Vegetative cuttings via stem.
*Time to produce a rooted young plant*.—28 days.
*Root description*.—Fine; roots, color is white RHS 155D.
*Rooting habit shape*.—Lanceolate.
*Plant form*.—Upright, bushy.
*Plant height*.—22.0 cm.
*Plant diameter or spread*.—35.0 cm.

Lateral branches/stems:
*Shape of the branch in cross-section*.—Circular.
*Hollowness of the branch*.—Present (very small hollowness, especially in older stem parts).
*Length*.—18.0 cm.
*Diameter*.—6.0 cm.
*Stem thickness*.—Thin.
*Internode length*.—3.0 cm to 4.5 cm.
*Internode quantity per branch*.—4-5.
*Number of internodes per branch/stem*.—4-5.
*Node length*.—0.4 cm.
*Node diameter*.—0.3 cm.
*Texture*.—Smooth.
*Color*.—RHS 138A.
*Flower clustering on the lateral branch*.—In some lateral branches.

Foliage:
*Arrangement*.—Opposite.
*Length*.—7.0 cm to 8.0 cm.
*Width*.—0.3 cm.
*Shape*.—Linear.
*Apex*.—Narrowly acute.
*Base*.—Round.
*Margin*.—Entire.
*Texture* (*both upper and lower surfaces*).—Smooth.
*Cross-section of the leaf*.—Weakly concave.
*Curvature of the leaf*.—Present.
*Glaucosity of the leaf*.—Weak.
*Leaf color* (*both immature and mature*).—Immature: Upper surface: RHS 137A. Lower surface: RHS 137B. Mature: Upper surface: RHS 137A. Lower surface: RHS 137B.
*Venation pattern*.—Absent.

Flowers:
*Flower type and habit*.—Single.
*Fragrance*.—Present, light sweet fragrance.
*Position of the flowers compared to the foliage of the plant*.—Same level.
*Profile of both the upper and lower part in the lateral view*.—Concave.
*Diameter of the flower*.—2.7 cm.
*Natural flowering season*.—Spring to autumn.
*Number of flowers per spray*.—2 to 3.
*Flower longevity on the plant*.—20 days.

Buds:
*Length*.—1.8 cm.
*Diameter*.—0.4 cm.
*Shape*.—Oblong.
*Color*.—Lower part RHS 139C, tip RHS 139A.
*Extrusion of the styles at the bud stage*.—Absent.

Corolla:
*Quantity of petals and arrangement*.—5 petals and arranged in several whorls.
*Corolla height*.—0.5 cm.
*Petal length*.—3 cm.
*Petal width*.—1.2 cm.
*Petal shape*.—Spoon shaped.
*Petal apex*.—Obtuse.
*Petal base*.—Acute.
*Petal margin*.—Dentate.
*Depth of petal margin*.—Medium.
*Petal texture* (*both upper and lower surfaces*).—Pubescent.
*Petal color*.—Immature: Upper surface: RHS 59A with RHS 65D border under low light, RHS 73A with RHS 59C star under high light conditions. Lower surface: RHS 62C. Mature: Upper surface: RHS 59A with RHS 65D border under low light, RHS 73A with RHS 59C star under high light conditions. Lower surface: RHS 62C.
*Macule*.—Absent.

Calyx:
*Quantity of sepals and arrangement*.—Composed of 5 sepals.
*Longitudinal axis of the lobes of the calyx*.—Straight.
*Shape*.—Cylindrical.
*Calyx height*.—1.8 cm.
*Calyx diameter* (*at the apex*).—0.4 cm.
*Sepal texture* (*both upper and lower surfaces*).—Smooth.
*Sepal color*.—Upper surface: RHS 139A. Lower surface: RHS 139C.
*Position of the outer lobes of the epicalyx in relation to the calyx*.—Adpressed and free.
*Apex shape of the outer lobes of the epicalyx*.—Medium acuminate.
*Tip length of the outer lobes of the epicalyx*.—0.3 cm.
*Apex shape of the inner lobes of the epicalyx*.—Short acuminate.
*Tip length of the inner lobes of the epicalyx*.—0.2 cm.

Peduncles:
*Length*.—3 cm.
*Diameter*.—0.15 cm.
*Strength*.—Medium.
*Texture*.—Smooth.
*Color*.—RHS 139A.

Reproductive organs:
*Stamens*.—None.
*Pistils*.—Quantity per flower: 2. Length: 1.2 cm. Diameter: 0.1 cm. Stigma: Color: RHS 77C. Shape: Filamentous. Length: 0.2 cm. Diameter: Less than 0.1 cm. Style: Color: RHS 155A. Length: 1.0 cm. Diameter: 0.1 cm. Number: Two. Shoulders: Not observed. Ovary: Color: RHS 145C. Width: 0.3 cm. Texture: Smooth.

Seeds: Yes.
*Color*.—RHS 200B to RHS 202A (Brown-black).
*Size*.—0.2 cm to 0.3 cm.
*Shape*.—Drop shaped.

Disease and insect resistance: No particular disease or insect resistance observed.

COMPARISON WITH PARENTAL LINE AND KNOWN VARIETY

'KLEDG23508' is distinguished from the female parent as described in Table 1.

TABLE 1

| Comparison with Parental Line | | |
|---|---|---|
| Trait or characteristic | 'KLEDG23508' | Female parent |
| Flower color | Dark purple with a light border | Pink with purple star in middle |

'KLEDG23508' can be compared to the commercial *Dianthus* variety 'KLEDG20336' (U.S. Plant Pat. No. 33,998). Differences between the varieties are described in Table 2.

TABLE 2

| Comparison with Similar Variety | | |
|---|---|---|
| Characteristic | 'KLEDG23508' | 'KLEDG20336' |
| Flower Color | Dark purple with a light border | Dark purple flower color with violet spots |

I claim:

1. A new and distinct cultivar of *Dianthus* Plant Named 'KLEDG23508', as illustrated and described herein.

* * * * *